US00PP20269P2

(12) United States Plant Patent
van der Spek

(10) Patent No.: US PP20,269 P2
(45) Date of Patent: Sep. 8, 2009

(54) ***HYDRANGEA* PLANT NAMED 'SIDASELM'**

(50) Latin Name: *Hydrangea macrophylla*
Varietal Denomination: Sidaselm

(76) Inventor: Daniel van der Spek, Nieuwkoopseweg 45, 2631 PP Nootdorp (NL)

( * ) Notice: Subject to any disclaimer, the term of this patent is extended or adjusted under 35 U.S.C. 154(b) by 26 days.

(21) Appl. No.: 11/903,299

(22) Filed: Sep. 22, 2007

(51) Int. Cl.
*A01H 5/00* (2006.01)

(52) U.S. Cl. ..... Plt./250
(58) Field of Classification Search ..... Plt./250
See application file for complete search history.

(56) References Cited

PUBLICATIONS

Pride of Place Plants–*Hydrangea* 'Sidaselm' http://www.prideofplaceplants.com/flowering_shrubs/hydrangea_selma.html.* http://web.archive.org/web.*

* cited by examiner

*Primary Examiner*—Annette H Para
*Assistant Examiner*—Louanne C Krawczewicz Myers

(57) ABSTRACT

A new and distinct *Hydrangea* cultivar named 'Sidaselm' is disclosed, characterized by light red flowers with white veins. The new variety is a *Hydrangea,* and naturally blooms from April through September.

1 Drawing Sheet

Latin name of the genus and species: *Hydrangea macrophylla.*
Variety denomination: 'Sidaselm'.

BACKGROUND OF THE INVENTION

The new cultivar is a product of a planned breeding program. The intent of this breeding program is to produce stronger pot plant varieties with attractive flower colors. The new variety was discovered as a seedling within the planned breeding program. This seedling is a result from the crossing of the female parent, an undistributed proprietary variety referred to as 9766 with the male parent, an undistributed proprietary variety referred to as 9822. The crossing was made by the inventor, Daniel van der Spek in the summer of 2000. 'Sidaselm' was selected by Daniel van der Spek in May of 2002 in Nootdorp, The Netherlands.

Asexual reproduction of the new cultivar 'Sidaselm' by vegetative cuttings was performed in Nootdorp, The Netherlands and has shown that the unique features of this cultivar are stable and reproduced true to type through 6 successive generations.

SUMMARY OF THE INVENTION

The cultivar 'Sidaselm' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Sidaselm'. These characteristics in combination distinguish 'Sidaselm' as a new and distinct *Hydrangea* cultivar:

1. Round mophead inflorescence;
2. Unique petal coloration of light red with white veins;
3. Dark green foliage;
4. Strong plant, resisting breaking in production and post-harvest situations.

Plants of the new cultivar 'Sidaselm' are similar to plants of the female parent, '9766' in most horticultural characteristics, however, plants of the new cultivar 'Sidaselm' has darker red flowers, more flowers per inflorescence, and a wider diameter inflorescence. Flowers of the new cultivar are distinctively light pink, while the female parent has light purple and white flower coloration and less flowers per inflorescence. 'Sidaselm' differs from the male parent '9822' in foliage color. Foliage of the new cultivar is darker than the male parent. Additionally, the new variety has foliage that is more resistant to stress.

Plants of the new cultivar 'Sidaselm' are similar to plants of the commercial variety 'Paris Rapa,' U.S. Plant Pat. No. 10,906. However, plants of the new cultivar 'Sidaselm' differ from 'Paris Rapa' in the following characteristics;

1. Foliage of 'Sidaselm' is much more resistant to stress than 'Paris Rapa.'
2. 'Sidaselm' has a wider inflorescence than 'Paris Rapa.'
3. 'Sidaselm' flowers are darker red.
4. 'Sidaselm' plants are taller than 'Paris Rapa.'
5. 'Sidaselm' plants produce roots faster than 'Paris Rapa.'

BRIEF DESCRIPTION OF THE PHOTOGRAPH

The accompanying photograph in FIG. 1 illustrates in full color a typical blooming plant of 'Sidaselm' grown in a greenhouse. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Sidaselm' plants grown in a greenhouse in Brielle, The Netherlands from October 2005 to October 2006. The growing temperature ranged from 16° C. to 17° C. at night to 18° C. to 20° C. during the day. The pH of the growing medium was between 5.0 and 5.5. Measurements and numerical values represent averages of typical flowering types.

Botanical classification: *Hydrangea macrophylla* cultivar 'Sidaselm'.

PROPAGATION

Time to rooting: 19 to 21 days at approximately 20° C.
Root description: Fine, fibrous.

PLANT

Growth habit: Flowering perennial shrub.
Height: Approximately 34 cm. from soil level to the top of the inflorescence.
Blooming period: Naturally blooming April through September.
Plant spread: Approximately 51.5 cm.
Growth rate: Moderate to Vigorous.
Branching characteristics: Moderately free branching.
Length of lateral branches: Approximately 27.3 cm.
Number of lateral branches: Approximately 14.
Diameter of lateral branches: Approximately 0.5 cm.
Pinching required: Yes.
*Details of pinching.*—The first pinch is given at 8 weeks from the planting of a rooted cutting. A second pinch is given 12 weeks from planting a rooted cutting.
Lateral branch shape: Round.
Lateral branch strength: Very strong.
Lateral branch texture: Leathery.
Lateral branch color: Approximately RHS Yellow-Green 144A, slightly tinged at the nodes with RHS Greyed-Purple 187C.
Other stem or plant characteristics: Stems covered with lenticels at a density of approximately 4.5 lenticels per square cm.
*Lenticel length.*—Approximately 0.15 cm.
*Lenticel width.*—Approximately 0.075 cm.
*Lenticel color.*—About RHS Greyed-Purple 186C.
Number of leaves per lateral branch: Average 6.
Age of plant described: Approximately 1 year.

FOLIAGE

Leaf:
*Arrangement.*—Opposite.
*Compound or single.*—Single.
*Average length.*—Approximately 10.8 cm.
*Average width.*—Approximately 7.3 cm.
*Shape of blade.*—Broad oval to broad elliptic oblong.
*Apex.*—Apiculate.
*Base.*—Acuminate.
*Attachment.*—Stalked.
*Margin.*—Serrate, approximately 3 teeth per cm.
*Texture of top surface.*—Moderately glossy, non-pubescent.
*Texture of bottom surface.*—Matte, non-pubescent.
*Leaf internode length.*—Approximately 8.6 cm.
*Color.*—Young foliage upper side: Near R.H.S. Green 141A, teeth tinged 186C. Young foliage under side: Near R.H.S. Green 143A. Mature foliage upper side: Near R.H.S. Green 139A. Mature foliage under side: Near R.H.S. Green 138A.
*Venation.*—Type: Pinnate. Venation color upper side: Near R.H.S. Yellow-Green 145C. Venation color under side: Near R.H.S. Yellow-Green 145B.
*Durability of foliage to stresses.*—High.
Petiole:
*Average length.*—Approximately 2.2 cm.
*Diameter.*—Approximately 0.4 cm.
*Color.*—Near R.H.S. Yellow-Green 145B.

FLOWER

Bloom period:
*Natural season.*—Continuous April through September.
Inflorescence:
*Arrangement.*—Terminal inflorescence.
*Type.*—Compound corymb.
*Height.*—Approximately 12.8 cm.
*Width.*—Approximately 17.0 cm.
*Quantity of flowers per inflorescence.*—Fertile flowers, approximately 60. Sterile Flowers, approximately 350.
Bud:
*Bud shape* (*sterile flowers*).—Obovate.
*Bud length* (*sterile flowers*).—Approximately 0.4 cm.
*Bud diameter* (*sterile flowers*).—Approximately 0.3 cm.
*Bud color* (*sterile flowers*).—Near R.H.S. Greyed-Purple 186D. Base/calyx: Near R.H.S. Yellow-Green 146C.
*Bud shape* (*fertile flowers*).—Globose.
*Bud length* (*fertile flowers*).—Approximately 0.5 cm.
*Bud diameter* (*fertile flowers*).—Approximately 0.5 cm.
*Bud color* (*fertile flowers*).—Near RHS Green-White 157A. Fertile flowers do not open.
Flower:
*Shape.*—Rotate.
*Facing direction.*—All directions, with the majority facing outward.
*Quantity of flowers per lateral stem.*—410.
*Quantity of flowers and buds per plant.*—Approximately 5700.
*Diameter of entire flower.*—Fertile; approximately 0.7 cm. Sterile: Approximately 4.1 cm.
*Depth of flower.*—Fertile; approximately 0.5 cm. Sterile: Approximately 1.2 cm.
*Rate of opening.*—Individual flowers: Fully open approximately 5 days from the bud stage. Fertile flowers do not open. Whole Plant: Approximately 50% of flowers open at once.
*Flower longevity on plant.*—Fertile flowers: Approximately 5 days. Sterile flowers: Approximately 35 days.
*Persistent or self-cleaning.*—Persistent.
*Fragrance.*—No.
Petals:
*Length of petal.*—Approximately 3.5 cm.
*Width of petal.*—Approximately 2.5 cm.
*Apex.*—Acute.
*Base.*—Cordate.
*Shape of petal.*—Ovate.
*Petal margin.*—Entire.
*Petal arrangement.*—Rotate.
*Petal number.*—Approximately 4.

*Petals fused.*—No.
*Petal appearance.*—Dull.
*Petal texture* (*both surfaces*).—Smooth.
Color:
*Upper surface at first opening.*—Near Red-Purple 57D, base slightly lighter with streaks of White 155C.
*Upper surface at maturity.*—Near Red-Purple 58B. Base: Near Red-Purple 57D with White 155B.
*Upper surface at fading.*—Near Red-Purple 57C. Base: Near Red-Purple 57D.
*Under surface at first opening.*—Near Red-Purple 57D.
*Under surface at maturity.*—Near Red-Purple 57C. Base: Near Red-Purple 57D.
*Under surface at facing.*—Near Red-Purple 57C. Base: Near Red-Purple 57D.
Petaloids: No.
Fragrance: None.

CALYX

Present: Yes.
Shape: Rotate, lower ⅔ fused.
Length: Approximately 0.3 cm.
Diameter: Approximately 0.35 cm.

SEPAL

Sepals: Only sterile flowers have sepals. Fertile flowers do not open.
Number: Average 5.
Sepal texture (both surfaces): Smooth.
Sepal arrangement: Rotate.
Sepal length: Approximately 0.3 cm.
Sepal width: Approximately 0.1 cm.
Sepal shape: Deltoid.
Base: Fused into a tube ⅔ of length.
Apex shape: Acute.
Margin: Entire.
Color: Upper side near R.H.S. Yellow-Green 146D. Under side near R.H.S. Yellow-Green 146C, base Yellow-Green 146D.

PEDUNCLE

Length: Approximately 9.8 cm.
Diameter: Approximately 0.35 cm.
Angle: Approximately 25 degrees (0 degrees=straight upright).
Strength: Strong.
Color: Near R.H.S. Yellow-Green 144B.

PEDICEL

Present: Yes.
Length (sterile flowers): Approximately 2.1 cm.
Diameter (sterile flowers): Approximately 1.5 cm.
Angle (sterile flowers): Approximately 5 degrees.
Strength (sterile flowers): Strong.
Color (sterile flowers): Near White 155A, base Greyed-Purple 187C.
Length (fertile flowers): Approximately 0.7 cm.
Diameter (fertile flowers): Approximately 0.3 cm.
Angle (fertile flowers): Approximately 10 degrees.
Strength (fertile flowers): Moderate.
Color (fertile flowers): Near Green-White 157A.

REPRODUCTIVE ORGANS

*Number of pistils per flower.*—3.
*Pistil length.*—Approximately 0.15 cm.
*Stigma shape.*—Lobed.
*Stigma color.*—Near Red-Purple 57D.
*Style color.*—Near Red-Purple 62D.
*Style length.*—Approximately 0.15 cm.
*Ovary color.*—Near Yellow-Green 154C.
*Stamens.*—Average 8.
*Anther shape.*—Broad kidney-shaped.
*Anther size.*—0.15 cm.
*Anther color.*—Near White 155A, filament colored Red-Purple 62C.
*Pollen color.*—Near White 155A.
*Pollen quantity.*—Very low.

OTHER CHARACTERISTICS

Disease resistance: Neither resistance nor susceptibility to diseases or pests has been observed in this variety.
Drought tolerance and cold tolerance: Semi-hardy perennial, tolerant of some high temperatures. Upper limit of temperature tolerance has not been observed, however, known to tolerate temperatures of at least up to 40° C. Lower limits have also not been observed, however, observed hardy to −15° C. No drought tolerance has been observed.
Fruit/seed production: No fruits/seeds detected to date.

What is claimed is:

1. A new and distinct cultivar of *Hydrangea* plant named 'Sidaselm' as herein illustrated and described.

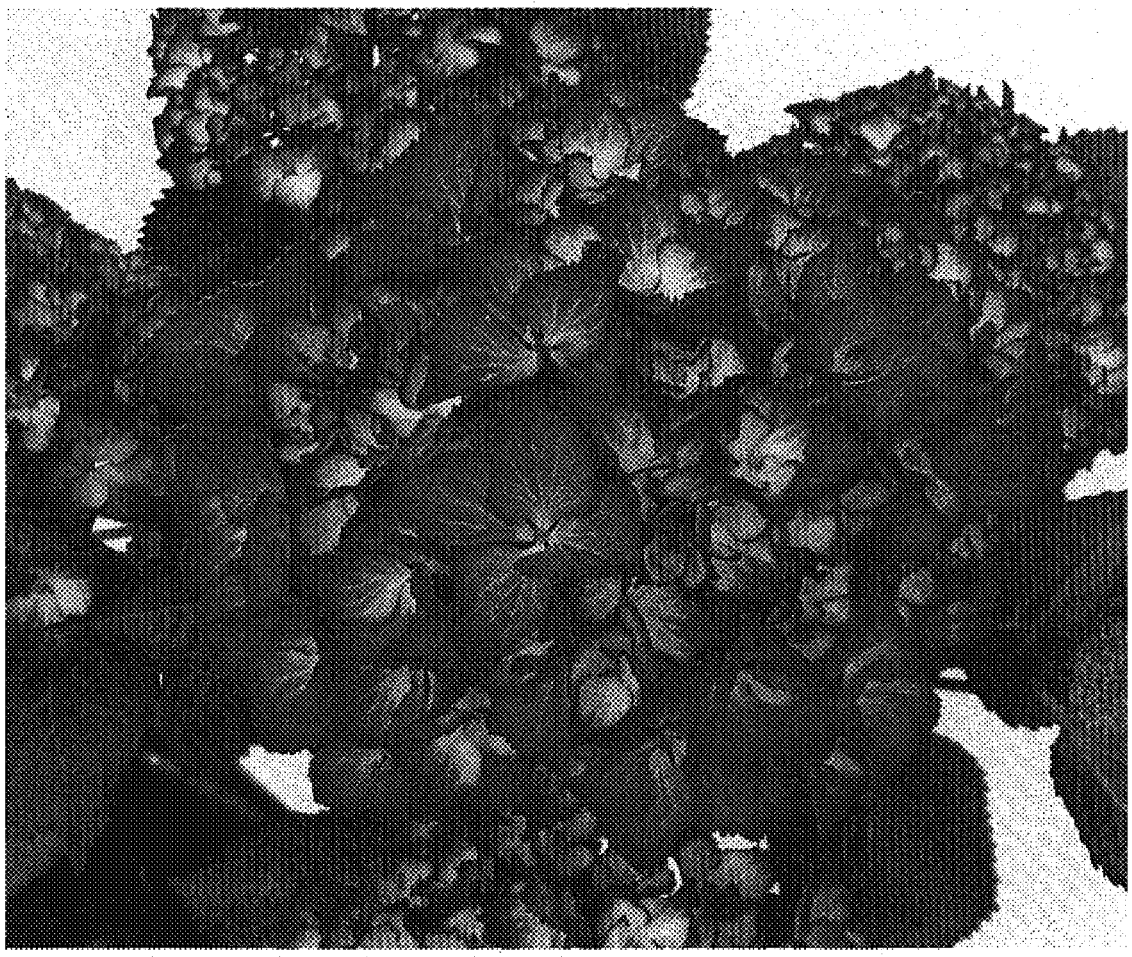

* * * * *